US006433163B1

(12) United States Patent
Ho

(10) Patent No.: US 6,433,163 B1
(45) Date of Patent: Aug. 13, 2002

(54) COMBINED SUPPORTED LIQUID MEMBRANE/STRIP DISPERSION PROCESS FOR THE REMOVAL AND RECOVERY OF PENICILLIN AND ORGANIC ACIDS

(75) Inventor: W. S. Winston Ho, Lexington, KY (US)

(73) Assignee: Commodore Separation Technoligies, Inc., New York, NY (US)

( * ) Notice: Subject to any disclaimer, the term of this patent is extended or adjusted under 35 U.S.C. 154(b) by 0 days.

(21) Appl. No.: 09/541,925

(22) Filed: Apr. 3, 2000

(51) Int. Cl.$^7$ .......................... C02F 1/00; C07D 499/18

(52) U.S. Cl. ...................... 540/315; 562/445; 562/580; 562/584; 562/600; 562/606; 562/608

(58) Field of Search ................................. 540/324, 341, 540/342, 346, 315; 562/445, 600, 580, 584, 606, 608

(56) References Cited

U.S. PATENT DOCUMENTS

| | | | | |
|---|---|---|---|---|
| 5,041,227 A | * | 8/1991 | van Eikeren et al. | ....... 210/640 |
| 5,507,949 A | * | 4/1996 | Ho | .............. 210/490 |
| 6,096,217 A | * | 8/2000 | Kilambi et al. | ............. 210/638 |
| 6,229,046 B1 | * | 5/2001 | Eyal et al. | ................... 562/589 |

OTHER PUBLICATIONS

Lee, C.J. et al, Biotech. Bioeng., 43, 1994, 309–313.*
Juang, R.S. et al, J. Mem. Sci., 137, 1997, 231–239.*
Juang, R.–S. et al, Ind. Eng. Chem.Res., 35, 1996, 1673–1679.*
Dozol, J.F, Casas J., and Sastre, A., "Stability of Flat Sheet Supported Liquid Membranes in the Transport of Radionuclides from Reprocessing Concentrate Solutions," *J. Membrane Sci.*, 82, 237–246 (1993).

Dreher, T.M. and Stevens, G.W., "Instability Mechanisms of Supported Liquid Membranes," *Sep. Sci. Technol.*, 33, 835–853 (1998).

Hano, T., Matsumoto, M., Kawazu, and Ohtake T., "Separation of Di– and Tripeptides with Solvent Extraction and an Emulsion Liquid Membrane," *J. Chem. Technol. Biotechnol.*, 62, 60–63 (1995).

Ho, Winston W. S., and Sirkar, Kamalesh, K., eds., *Membrane Handbook*, Chapman & Hall, New York, 595–912 (1992).

Itoh, H., Thien, M.P., Hatton, T.A., and Wang, D.I.C., "Water Transport Mechanism in Liquid Emulsion Membrane Process for the Separation of Amino Acids," *J. Membrane Sci.*, 51, 309–322 (1990).

Ju, L.K., and Verma A., "Characteristics of Lactic Acid Transport in Supported Liquid Membranes" *Sep. Sci. Technol.*, 29, 2299–2315 (1994).

Juang, R.S., and Lin, Y.S., "Investigation of Interfacial Reaction Kinetics of Penicillin G and Amberlite LA–2 from Membrane Flux Measurements," *J. Membrane Sci.±*, 141, 19–30 (1998).

Juan, R.S., and Chen, L.J., "Analysis of the Transport Rates of Citric Acid through a Supported Liquid Membrane Containing Tri–n–octylamine," *Ind. Eng. Chem. Res.*, 1673–1679, (1996).

(List continued on next page.)

Primary Examiner—Mukund J. Shah
Assistant Examiner—Thomas C. McKenzie
(74) Attorney, Agent, or Firm—Kilpatrick Stockton LLP

(57) ABSTRACT

The present invention provides a novel process for the removal and recovery of penicillin and organic acids from process streams and waste waters. The process of the present invention utilizes a combination of a supported liquid membrane (SLM) and a strip dispersion to improve extraction of the penicillin and organic acids while increasing membrane stability and reducing processing costs.

15 Claims, 2 Drawing Sheets

OTHER PUBLICATIONS

Juang, R.S., Lee, S.H., and Shiau, R.C., "Mass–transfer Modeling of Permeation of Lactic Acid across Amine–mediated Supported Liquid Membranes," *J. Membrane Sci.*, 137, 231–239 (1997).

Juang, R.S., Lee, S.H., and Huang, R.H., "Modeling of Amine–Facilitated Liquid Membrane Transport of Binary Organic Acids," *Sep. Sci. Technol.*, 33, 2379–2395 (1998).

Kemperman, A. J. B., Bargeman, D., Van Den Boomgaard, Th., Strathmann, H., "Stability of Supported Liquid Membranes: State of Art," *Sep. Sci. Technol.*, 31, 2733 (1996).

Lee, C.J., Yeh, H.J., Yang, W.Y., and Kan, C.R., "Separation of Penicillin G from Phenylacetic Acid in a Supported Liquid Membrane System," *Biotechnol. Bioeng.*, 43, 309–313 (1994).

Lee, K.H., Lee, S.C., and Lee, W.K., "Penicillin G Extraction from Model Media Using an Emulsion Liquid Membrane: A Theoretical Model of Product Decomposition," *J. Chem. Technol. Biotechnol.*, 59, 365–370 (1994).

Lee, K.H., Lee, S.C., and Lee, W.K., "Penicillin G Extraction from Model Media Using an Emulsion Liquid Membrane: Determination of Optimum Extraction Conditions," *J. Chem. Technol. Biotechnol.*, 59, 371–376 (1994).

Lee, S.C., Lee, K.H., Hyun, G. H., and Lee, W.K., "Continuous Extraction of Penicillin G by an Emulsion Liquid Membrane in a Countercurrent Extraction Column," *J. Membrance Sci.*, 124, 43–51 (1997).

Lee, S.C., Chang, J. H., Ahn, B.S. Lee, W.K., "Mathematical Modeling of Penicillin G Extraction in an Emulsion Liquid Membrane System Containing only a Surfactant in the Membrane Phase," *J. Membrane Sci.*, 149, 39–49 (1998).

Lee, S.C., "Effect of Volume Ratio of Internal Aqueous Phase to Organic Membrane Phase (W/O Ratio) of Water–in–Oil Emulsion on Penicillin G Extraction by Emulsion Liquid Membrane," *J. Membrane Sci.*, 163, 193–201 (1999).

Liu, X. R., and Liu, D.S., "Modeling of Facilitated Transport of Phenylalanine by Emulsion Liquid Membranes with Di(2–ethylhexyl) Phosphoric Acid as a Carrier," *Sep. Sci. Technol.*, 33, 2597–2608 (1998).

Matsumoto, M., Ohtake, T., Hirata, M. and Hano, T., "Extraction Rates of Amino Acids by an Emulsion Liquid Membrane with Tri–n–octylmethylammonium Chloride," *J. Chem. Technol. Biotechnol.*, 73, 237–242, (1998).

Mok, Y.S., Lee, S.C., and Lee, W.K., "Synergistic Effect of Surfactant on Transport Rate of Organic Acid in Liquid Emulsion Membranes," *Sep Sci. Technol.*, 30, 399–417 (1995).

O'Brien, D. J. and Senske G.E., "Separation and Recovery of Low Molecular Weight Organic Acids by Emulsion Liquid Membranes," *Sep. Sci. Technol.*, 24, 617–628 (1989).

Ozadali, F., Glatz, B. A., and Glatz, C.E., "Fed–batch Fermentation with and without On–line Extraction forPropionic and Acetic Acid Production by Propionibacterium Acidipropionici," *Applied Microb Biotechnol.*, 44, 710–716 (1996).

Pickering, P. J., and Chaudhuri, J.B., "Enantioselective Extraction of D–Phenylalanine from Racemic D– and L–Phenylalanine Using Chiral Emulsion Liquid Membranes," *J. Membrane Sci.*, 127 115–130 (1997).

Raghuraman, B., and Wiencek, J., "Extraction with Emulsion Liquid Membranes in a Hollow–Fiber Contractor," *AIChEJ.*, 39, 1885–1889 (1993).

Rockman, J.T., Kehat, E., and Lavie, R., "Mathematical Model for Thermally Enhanced Facilitated Transport," *Ind. Eng. Chem. Res.*, 34, 2455–2463 (1995).

Scheper, T., Likidis, Z., Makryaleas, K., Nowattny, Ch., Schugerl, K., "Three Different Examples of Enzymatic Bioconversion in Liquid Membrane Reactors," *Enzyme Microb. Technol.*, 9, 625–361 (1987).

Thien, M. P. and Hatton, T.A., "Liquid Emulsion Membranes and Their Applications in Biochemical Processing," *Sep. Sci., Technol.*, 23, 819–853 (1998).

* cited by examiner

COMBINED SUPPORTED LIQUID MEMBRANE/STRIP DISPERSION PROCESS FOR THE REMOVAL AND RECOVERY OF PENICILLIN AND ORGANIC ACIDS

FIELD OF THE INVENTION

The present invention relates to the removal and recovery of penicillin and organic acids from feed solutions, such as process streams and waste waters, using supported liquid membrane technology.

BACKGROUND OF THE INVENTION

Liquid membranes combine extraction and stripping into one step, rather than the two separate steps required in conventional processes such as solvent extractions. A one-step liquid membrane process provides the maximum driving force for the separation of a targeted species, leading to the best clean-up and recovery of the species (W. S. Winston Ho and Kamalesh K. Sirkar, eds., *Membrane Handbook*, Chapman & Hall, New York, 1992).

There are two types of liquid membranes: (1) supported liquid membranes (SLMs) and (2) emulsion liquid membranes (ELMs). In SLMs, the liquid membrane phase is the organic liquid imbedded in pores of a microporous support, e.g., microporous polypropylene hollow fibers (W. S. Winston Ho and Kamalesh K. Sirkar, eds., *Membrane Handbook*, Chapman & Hall, New York, 1992). When the organic liquid contacts the microporous support, it readily wets the pores of the support, and the SLM is formed.

For the extraction of a target species from a feed solution, the organic-based SLM is placed between two aqueous solutions—the feed solution and the strip solution where the SLM acts as a semi-permeable membrane for the transport of the target species from the feed solution to the strip solution. The organic liquid in the SLM is immiscible in the aqueous feed and strip streams and contains an extractant, a diluent, and sometimes a modifier. The diluent is generally an inert organic solvent.

The use of SLMs to remove penicillin and organic acids from aqueous feed solutions has attracted considerable attention in the scientific and industrial community. The extraction of penicillin G from aqueous feed solutions has been investigated (C. J. Lee, H. J. Yeh, W. Y. Yang, and C. R. Kan, "Preparation of penicillin G from Phenylacetic Acid in a Supported Liquid Membrane System", *Biotechnol. Bioeng.*, 43, 309–313 (1994); R. S. Juang and Y. S. Lin, "Investigation on Interfacial Reaction Kinetics of Penicillin G and Amberlite LA-2 from Membrane Flux Measurements", *J. Membrane Sci.*, 141, 19–30 (1998)).

The extraction of organic acids, including phenylalanine, acrylic acid, lactic acid, proprionic acid, citric acid, and acetic acid, from aqueous solutions with SLMs has been studied (L. K. Ju and A. Verma, "Characteristics of Lactic Acid Transport in Supported Liquid Membranes", *Sep. Sci. Technol.*, 29, 2299–2315 (1994); J. T. Rockman, E. Kehat, and R. Lavie, "Mathematical Model for Thermally Enhanced Facilitated Transport", *Ind. Eng. Chem. Res.*, 34, 2455–2463 (1995); F. Ozadali, B. A. Glatz, and C. E. Glatz, "Fed-batch Fermentation with and without On-line Extraction for Propionic and Acetic Acid Production by Propionibacterium Acidipropionici", *Applied Microb. Biotechnol.*, 44 710–716 (1996); R. S. Juang and L. J. Chen, "Analysis of the Transport Rates of Citric Acid through a Supported Liquid Membrane Containing Tri-n-octylamine", *Ind. Eng. Chem. Res.*, 35, 1673–1679 (1996); R. S. Juang, S. H. Lee, and R. C. Shiau, "Mass-transfer Modeling of Permeation of Lactic Acid across Amine-mediated Supported Liquid Membranes", *J. Membrane Sci.*, 137, 231–239 (1997); R. S. Juang, S. H. Lee, and R. H. Huang, "Modeling of Amine-facilitated Liquid Membrane Transport of Binary Organic Acids, *Sep. Sci. Technol.*, 33, 2379–2395 (1998)).

One disadvantage of SLMs is their instability due mainly to loss of the membrane liquid (organic solvent, extractant, and/or modifier) into the aqueous phases on each side of the membrane (A. J. B. Kemperman, D. Bargeman, Th. Van Den Boomgaard, H. Strathmann, "Stability of Supported Liquid Membranes: State of the Art", *Sep. Sci. Technol.*, 31, 2733 (1996); T. M. Dreher and G. W Stevens, "Instability Mechanisms of Supported Liquid Membranes", *Sep. Sci. Technol.*, 3, 835–853 (1998); J. F. Dozol, J. Casas, and A. Sastre, "Stability of Flat Sheet Supported Liquid Membranes in the Transport of Radionuclides from Reprocessing Concentrate Solutions", *J. Membrane Sci.*, 82, 237–246 (1993)). The prior art has attempted to solve this problem through the combined use of SLM with a module containing two sets of hollow fibers, i.e., the hollow-fiber contained liquid membrane (W. S. Winston Ho and Kamalesh K. Sirkar, eds., *Membrane Handbook*, Chapman & Hall, New York, 1992). In this configuration with two sets of microporous hollow-fiber membranes, one carries the aqueous feed solution, and the other carries the aqueous strip solution. The organic phase is contained between the two sets of hollow fibers by maintaining the aqueous phases at a higher pressure than the organic phase. The use of the hollow-fiber contained liquid membrane increases membrane stability, because the liquid membrane can be continuously replenished. However, this configuration is not advantageous because it requires mixing two sets of fibers to achieve a low contained liquid membrane thickness.

In ELMs, an emulsion acts as a liquid membrane for the separation of the target species from a feed solution. An ELM is created by forming a stable emulsion, such as a water-in-oil emulsion, between two immiscible phases, followed by dispersion of the emulsion into a third, continuous phase by agitation for extraction. The membrane phase is the oil phase that separates the encapsulated, internal aqueous droplets in the emulsion from the external, continuous phase (W. S. Winston Ho and Kamalesh K. Sirkar, eds., *Membrane Handbook*, Chapman & Hall, New York, 1992). The species-extracting agent is contained in the membrane phase, and the stripping agent is contained in the internal aqueous droplets. Emulsions formed from these two phases are generally stabilized by use of a surfactant. The external, continuous phase is the feed solution containing the target species. The target species is extracted from the aqueous feed solution into the membrane phase and then stripped into the aqueous droplets in the emulsion. The target species can then be recovered from the internal aqueous phase by breaking the emulsion, typically via electrostatic coalescence, followed by electroplating or precipitation.

The use of ELMs to remove penicillin and organic acids from aqueous feed solutions has long been pursued in the scientific and industrial community. The use of ELMs for the extraction of Penicillin G from aqueous feed solutions has been described (T. Scheper, Z. Likidis, K. Makryaleas, Ch. Nowattny, and K. Schugerl, "Three Different Examples of Enzymatic Bioconversion in Liquid Membrane Reactors", *Enzyme Microb. Technol.*, 2, 625–631 (1987); K. H. Lee, S. C. Lee, and W. K. Lee, "Penicillin G Extraction from Model Media Using an Emulsion Liquid Membrane: A Theoretical Model of Product Decomposition", *J. Chem. Technol. Biotechnol.*, 59, 365–370 (1994); K. H. Lee, S. C. Lee, and W. K. Lee, "Penicillin G Extraction from Model Media Using an Emulsion Liquid Membrane: Determination of Optimum Extraction Conditions, *J. Chem. Technol. Biotechnol.*, 59, 371–376 (1994); Y. S. Mok, S. C. Lee, and W. K. Lee, "Synergistic Effect of Surfactant on Transport Rate of Organic Acid in Liquid Emulsion Membranes", *Sep. Sci. Technol.*, 30, 399–417 (1995); S. C. Lee, K. H. Lee, G. H. Hyun, and W. K. Lee, "Continuous Extraction of Penicillin G by an Emulsion Liquid Membrane in a Countercurrent Extraction Column", *J. Membrane Sci.*, 124, 43–51 (1997); S. C. Lee, J. H. Chang, B. S. Ahn, and W. K. Lee, "Mathematical Modeling of Penicillin G Extraction in an Emulsion Liquid Membrane System Containing only a Surfactant in the Membrane Phase", *J. Membrane Sci.*, 149, 39–49 (1998); S. C. Lee, "Effect of Volume Ratio of Internal Aqueous Phase to Organic Membrane Phase (W/O Ratio) of Water-in-Oil Emulsion on Penicillin G Extraction by Emulsion Liquid Membrane", *J. Membrane Sci.*, 163, 193–201 (1999)).

The extraction of organic acids, including phenylalanine, acrylic acid, lactic acid, proprionic acid, citric acid, and acetic acid, from aqueous solutions with ELMs has been investigated (M. P. Thien and T. A. Hatton, "Liquid Emulsion Membranes and Their Applications in Biochemical Processing", *Sep. Sci. Technol.*, 23, 819–853 (1988); D. J. O'Brien and G. E. Senske, "Separation and Recovery of Low Molecular Weight Organic Acids by Emulsion Liquid Membranes", *Sep. Sci. Technol.*, 24, 617–628 (1989); H. Itoh, M. P. Thien, T. A. Hatton, and D. I. C. Wang, "Water Transport Mechanism in Liquid Emulsion Membrane Process for the Separation of Amino Acids", *J. Membrane Sci.*, 51, 309–322 (1990); T. Hano, M. Matsumoto, T. Kawazu, and T. Ohtake, "Separation of Di- and Tripeptides with Solvent Extraction and an Emulsion Liquid Membrane", *J. Chem. Technol. Biotechnol.*, 62, 60–63 (1995); P. J. Pickering and J. B. Chaudhuri, "Enantioselective Extraction of D-Phenylalanine from Racemic D- and L-Phenylalanine Using Chiral Emulsion Liquid Membranes", *J. Membrane Sci.*, 127, 115–130 (1997); M. Matsumoto, T. Ohtake, M. Hirata, and T. Hano, "Extraction Rates of Amino Acids by an Emulsion Liquid Membrane with Tri-n-octylmethylammonium Chloride", *J. Chem. Technol. Biotechnol.*, 73, 237–242 (1998); X. R. Liu and D. S. Liu, "Modeling of Facilitated Transport of Phenylalanine by Emulsion Liquid Membranes with Di(2-ethylhexyl) Phosphoric Acid as a Carrier", *Sep. Sci. Technol.*, 33, 2597–2608 (1998)).

One disadvantage of ELMs is that the emulsion swells upon prolonged contact with the feed stream. This swelling causes a reduction in the stripping reagent concentration in the aqueous droplets which reduces stripping efficiency. It also results in dilution of the target species that has been concentrated in the aqueous droplets, resulting in lower separation efficiency of the membrane. The swelling further results in a reduction in membrane stability by making the membrane thinner. Finally, swelling of the emulsion increases the viscosity of the spent emulsion, making it more difficult to demulsify. A second disadvantage of ELMs is membrane rupture, resulting in leakage of the contents of the aqueous droplets into the feed stream and a concomitant reduction of separation efficiency. Raghuraman and Wiencek (B. Raghuraman and J. Wiencek, "Extraction with Emulsion Liquid Membranes in a Hollow-Fiber Contactor", *AIChE J.*, 39, 1885–1889 (1993)) have described the use of microporous hollow-fiber contactors as an alternative contacting method to direct dispersion of ELMs to minimize the membrane swelling and leakage. This is due to the fact that the hollow-fiber contactors do not have the high shear rates typically encountered with the agitators used in the direct dispersion. Additional disadvantages include the necessary process steps for making and breaking the emulsion.

Thus, there is a need in the art for an extraction process which maximizes the stability of the SLM membrane, resulting in efficient removal and recovery of penicillin or organic acids from the aqueous feed solutions.

SUMMARY OF THE INVENTION

The present invention relates generally to a process for the removal and recovery of target species from a feed solution using combined SLM/strip dispersion. The invention also relates to a process resulting in efficient removal and recovery of penicillin and organic acids from process streams and waste water.

It must be noted that, as used in this specification and the appended claims, the term penicillin shall be inclusive of all members of the group of antibiotics biosynthesized by several species of molds and any synthetic derivatives.

In one embodiment, the present invention relates to a process for the removal and recovery of penicillin and organic acids from a feed solution which comprises the following steps. First, a feed solution containing penicillin or organic acids is passed on one side of the SLM embedded in a microporous support material to remove the penicillin or organic acids by the use of a strip dispersion on the other side of the SLM. As described above, the strip dispersion can be formed by dispersing an aqueous strip solution in an organic liquid, for example, using a mixer. The strip dispersion, or a part of the strip dispersion, is then allowed to stand, resulting in separation into two phases: the organic liquid phase and the aqueous strip solution phase containing a concentrated solution of the target species.

The continuous organic phase of the strip dispersion readily wets the pores of a microporous support to form a stable SLM. The process of the present invention provides a number of operational and economic advantages over the use of conventional SLMs.

Thus, it is an object of the present invention to provide an SLM process for the removal and recovery of target species which provides increased membrane stability.

It is another object of the invention to provide an SLM process having improved flux.

It is yet another object of the present invention to provide an SLM process having improved recovery of the target species to provide a concentrated strip solution.

It is a further object of the invention to provide an SLM process for the removal and recovery of a target species from a feed solution which exhibits decreased operation costs and a decreased capital investment over conventional SLM processes.

DESCRIPTION OF THE PREFERRED EMBODIMENTS

The present invention relates to a process for the removal and recovery of target species from a feed solution, such as process streams or waste waters. These target species include, but are not limited to, penicillin such as penicillin G and penicillin V, and organic acids, such as phenylalanine, acrylic acid, lactic acid, proprionic acid, citric acid, and acetic acid. This new process employs a combination of a supported liquid membrane (SLM) and a strip dispersion.

In one embodiment, the present invention relates to a process for the removal and recovery of penicillin from a feed solution which comprises the following steps. First, a feed solution containing penicillin is passed on one side of the SLM embedded in a microporous support material and treated to remove the penicillin by the use of a strip dispersion on the other side of the SLM. The strip dispersion can be formed by dispersing an aqueous strip solution in an organic liquid, for example, using a mixer. Second, the strip dispersion, or a part of the strip dispersion, is allowed to stand, resulting in separation of the dispersion into two phases: the organic liquid phase and the aqueous strip solution phase containing a concentrated solution of the target species.

In another embodiment the present invention relates to a process for the removal and recovery of organic acids from a feed solution which comprises the following steps. First, a feed solution containing organic acids is passed on one side of the SLM embedded in a microporous support material and treated to remove the organic acid by the use of a strip dispersion on the other side of the SLM. The strip dispersion can be formed by dispersing an aqueous strip solution in an organic liquid, for example, using a mixer. Second, the strip dispersion, or a part of the strip dispersion, is allowed to stand, resulting in separation of the dispersion into two phases: the organic liquid phase and the aqueous strip solution phase containing a concentrated solution of the target species.

Figure 1:
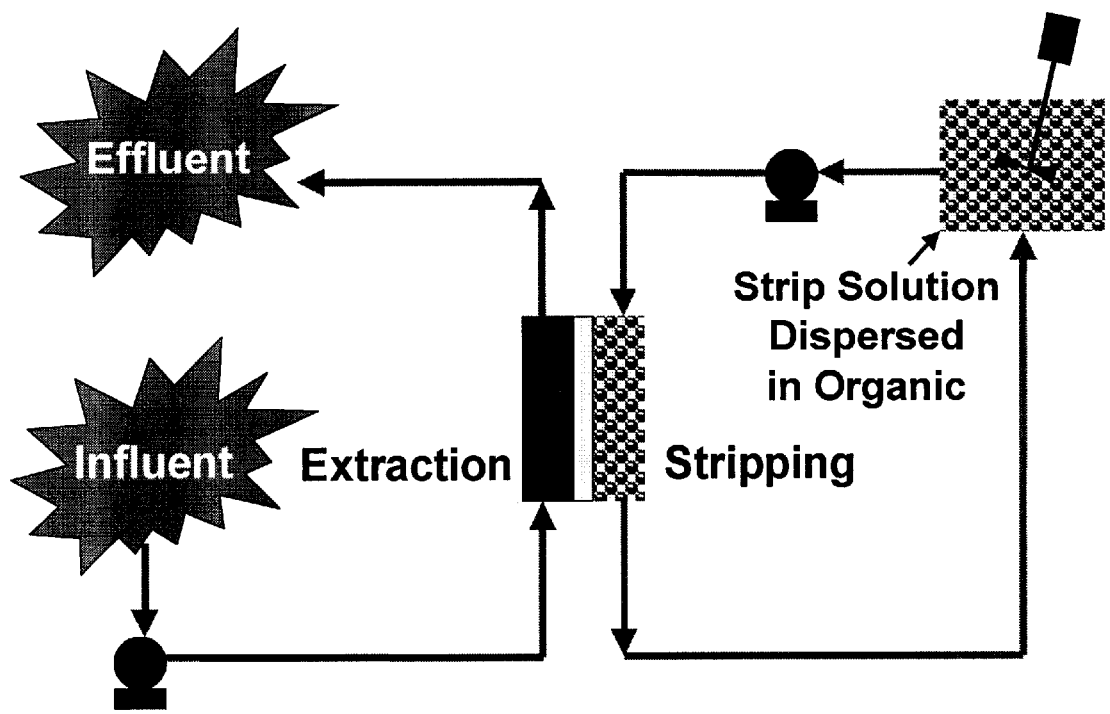
FIG. 1 is a schematic representation of the combined supported liquid membrane/strip dispersion of the present invention.

While any SLM configuration can be employed in the process of the invention, the preferred configuration employs a hollow fiber module as the liquid membrane microporous support. Such hollow fiber modules consist of microporous hollow fibers arranged in a shell-and-tube configuration. In the present invention, the strip dispersion is passed through either the shell side of the module or the tube side of the module, and the aqueous feed solution containing the target species for extraction is passed through the opposing side of the module. The use of the hollow fiber system in the combined SLM/strip dispersion process allows continuous replenishment of the strip dispersion as shown in FIG. 1, ensuring a stable and continuous operation.

For the purposes of the invention, strip dispersion is defined as a mixture of an aqueous phase and an organic phase. The aqueous phase of the dispersion comprises an aqueous strip solution, while the organic phase comprises one or more extractants in an organic liquid. The dispersion is formed by the mixing of the two phases as shown in FIG. 1. This combination results in droplets of the aqueous strip solution in a continuous organic phase. The dispersion is maintained during the extraction process due to the flow of the dispersion through a membrane module, e.g., a hollow-fiber module. The continuous organic phase of the strip dispersion readily wets the hydrophobic pores of the microporous hollow fibers in the module, forming a stable liquid membrane.

Figure 2:
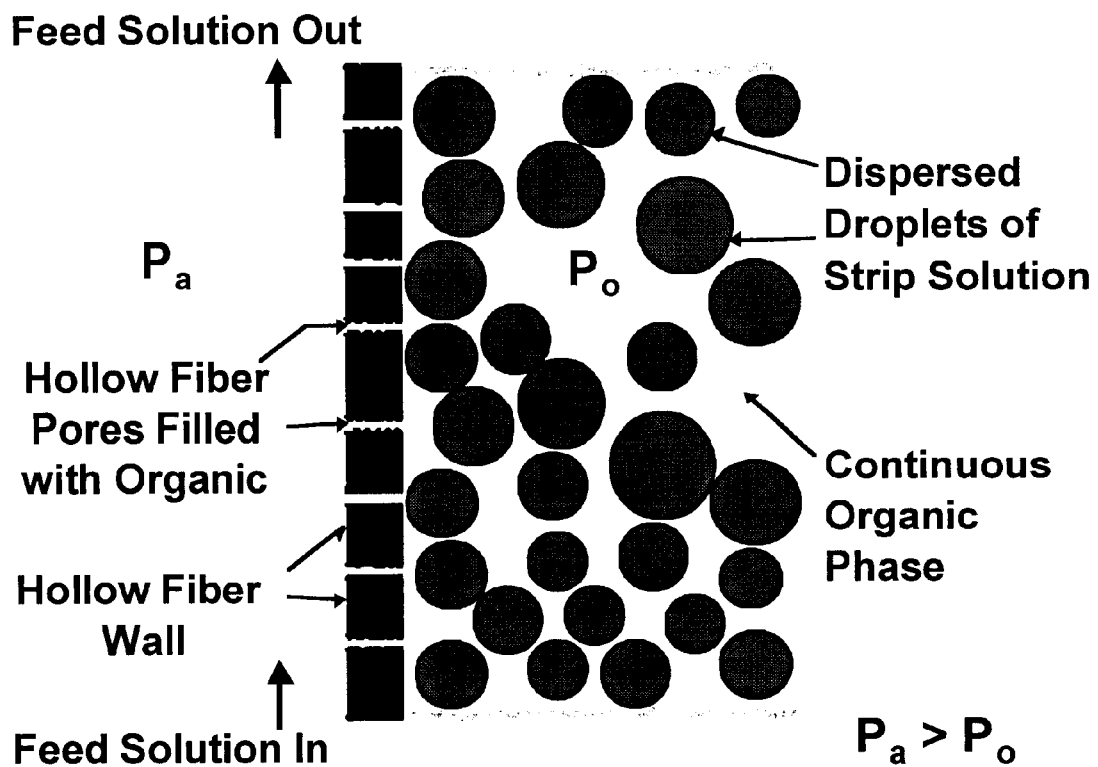
FIG. 2 is an enlarged view of the schematic representation of the combined supported liquid membrane/strip dispersion of the present invention.

FIG. 2 shows an enlarged view of a schematic representation of the SLM with strip dispersion of the present invention. A low pressure, $P_a$, which is typically less than approximately 10 psi, is applied on the feed solution side of the SLM. The pressure, $P_a$ is greater than the pressure $P_o$ on the strip dispersion side of the SLM. This difference in pressure prevents the organic solution of the strip dispersion from passing through the pores to come into the feed solution side. The dispersed droplets of the aqueous strip solution typically range in size from about 80 micrometers to about 800 micrometers. This size range is orders of magnitude larger than the pore size of the microporous polypropylene support employed for the SLM, which is approximately 0.03 micrometer. Thus, these droplets are retained on the strip dispersion side of the SLM and cannot pass through the pores to go to the feed solution side.

In this SLM/strip dispersion system, there is a constant supply of the organic membrane solution, i.e. the organic phase of the strip dispersion, into the pores. This constant supply of the organic phase ensures a stable and continuous operation of SLM. In addition, the direct contact between the organic and strip phases provides for efficient mass transfer for stripping. The organic and strip phases can be mixed, for example, with high-shear mixing, to increase the contact between the two phases.

Once the removal of the target species is complete, the mixer for the strip dispersion is stopped, and the dispersion is allowed to stand until it separates into the two phases, the organic membrane solution and the concentrated strip solution. The concentrated strip solution is the product of this process.

The feed solution includes, but is not limited to, process streams and waste waters containing penicillin and organic acids. Penicillins that can be extracted by the present process include, but are not limited to, penicillin G and penicillin V. Organic acids include, but are not limited to, phenylalanine, acrylic acid, lactic acid, proprionic acid, and acetic acid.

The microporous support employed in the invention is comprised of, for example, microporous polypropylene, polytetrafluoroethylene, polyethylene, polysulfone, polyethersulfone, polyetheretherketone, polyimide, polyamide, or mixtures thereof. The preferred microporous support is microporous polypropylene hollow fibers.

The aqueous portion of the strip dispersion comprises an aqueous base solution. Examples of bases useful in the present invention include, but are not limited to, sodium carbonate ($Na_2CO_3$), sodium bicarbonate ($NaHCO_3$), sodium hydroxide (NaOH), ammonium hydroxide ($NH_4OH$), and tetramethylammonium hydroxide (($CH)_4NOH$). The base is advantageously present in a concentration between about 0.01 M and about 16 M, more preferably between about 0.2 M and about 2M.

The continuous organic liquid phase into which the aqueous strip solution is dispersed contains one or more extractants. Any extractant capable of extracting the target species contained in the feed solution can be used in the present invention. Typical extractants that are known in the art for extraction of penicillin or organic acid from process streams or waste waters can be employed in the present strip dispersion. Examples of such extractants are those disclosed in the references listed in the background section. Selection of such extractants based upon the specific target species to be extracted is within the level of skill in the art.

The organic liquid of the present strip dispersion optionally comprises a hydrocarbon solvent or solvent mixture. The hydrocarbon solvent or mixture has a number of carbon atoms per solvent molecule ranging from about 6 to about 18, preferably from about 10 to about 14. Hydrocarbon solvents that are useful in the present invention include, for example, n-decane, n-undecane, n-dodecane, n-tridecane, n-tetradecane, isodecane, isoundecane, isododecane, isotridecane, isotetradecane, isoparaffinic hydrocarbon solvent (for example, with a flash point of 92° C., a boiling point of 254° C., a viscosity of 3 cp (at 25° C.), and a density of 0.791 g/ml (at 15.6° C.)) or mixtures of these solvents.

The organic liquid of the present strip dispersion optionally contains a modifier to enhance the complexation and/or stripping of the target species. The modifier can be, for example, an alcohol, a nitrophenyl alkyl ether, a trialkyl phosphate or mixtures of these compounds. Examples of alcohols that can be used are hexanol, heptanol, octanol, nonanol, decanol, undecanol, dodecanol, tridecanol, tetradecanol, pentadecanol, hexadecanol, heptadecanol, octadecanol or mixtures thereof. Examples of nitrophenyl ethers that can be used are o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether or mixtures thereof. The trialkyl phosphate can be, for example, tributyl phosphate, tris(2-ethylhexyl) phosphate or mixtures thereof.

The organic liquid of the present strip dispersion comprises about 2% to about 100% (approximately about 0.05M to about 3M) extractant and about 0% to about 20% modifier in a hydrocarbon solvent or mixture. More preferably, the organic liquid of the present strip dispersion comprises about 5% to about 40% extractant and about 1% to about 10% modifier in a hydrocarbon solvent or mixture. Even more preferably, the organic liquid comprises about 5% to about 40% extractant and about 1% to about 10% dodecanol in an isoparaffinic hydrocarbon solvent or in n-dodecane. All percentages are by weight unless specified otherwise.

The present invention has several advantages over conventional SLM technology. These advantages include increased membrane stability, reduced costs, increased simplicity of operation, improved flux, and improved recovery of target species concentration. The present invention has several advantages over conventional SLM technology. These advantages include increased simplicity of operation, reduction of capital and operation costs, and increased efficiency of target species removal.

The present invention provides a constant supply of the organic membrane solution into the pores of the hollow fiber support. This constant supply results in an SLM which is more stable than conventional SLMs, ensuring a stable and continuous operation. The constant supply also eliminates the need for recharging membrane modules which is required with conventional SLMs. It also eliminates the need for a second set of membrane modules for use during recharging of the first set of membrane modules. Thus, the present invention decreases not only the operational costs but also the initial capital investment in the system. The present invention also increases simplicity of the removal operation. The present invention provides direct contact between the organic/extraction and aqueous strip phase. The mixing of these phases provides an extra mass transfer surface area in addition to the area given by the hollow fibers, leading to extremely efficient stripping of the target species from the organic phase. This efficient strip ping enhances the flux for the extraction of many targeted species, resulting in unexpectedly high flux results as compared with conventional SLM extractions.

The present invention comprises a new type of SLM which provides increased flexibility of aqueous strip/organic volume ratio. This flexibility allows the use of a smaller volume of aqueous strip solution to obtain a higher concentration of the recovered species in the aqueous strip solution. The concentrated strip solution is a valuable product for resale or reuse.

This invention is further illustrated by the following examples, which are not to be construed in any way as imposing limitations upon the scope thereof. To the contrary, it is to be clearly understood that resort can be had to various other embodiments, modifications, and equivalents thereof which, after reading the description herein, can suggest themselves to those skilled in the art without departing from the spirit of the present invention and/or the scope of the appended claims.

EXAMPLES

GENERAL PROCEDURE

The strip dispersion for each of the following examples was prepared by mixing an aqueous strip solution in a quantity, for example, 200 ml, of an organic extractant solution. The organic extractant solution can be, for example, Isopar L, an isoparaffinic hydrocarbon solvent with a flash point of 62° C., a boiling point of 207° C., a viscosity of 1.5 cp (at 25° C.), and a density of 0.767 g/ml (at 15.6° C.), containing 1 wt. % o-nitrophenyl octyl ether (o-NPOE) and 10 wt. % N-lauryl-N-trialkylmethylamine with a molecular weight of 372 (or a total number of 25.3 carbon atoms per amine molecule, e.g., Amberlite LA-2). A quantity of combined aqueous strip solution/organic extractant solution, for example, 800 ml, was introduced into a Fisher brand mixer with a 2-inch diameter, 6-bladed, high-shear impeller at 500 rpm as measured by Ono Sokki HT-4100 tachometer. The mixer was plugged into a varistat to allow for adjustable speed control. The impeller was initially started at 50% of the full power and varistat at 80%.

All of the following examples were run in countercurrent fashion with the feed solution passed through the tube side of the microporous polypropylene hollow-fiber module. The microporous polypropylene hollow-fiber module of 2.5 inches in diameter and 8 inches in length, providing a surface area of 1.4 square meters. The process was first started by passing water through the hollow fiber module. Once pressures were adjusted and stable, the water was then replaced with the feed solution. A positive pressure was maintained on the feed side to prevent the organic phase in the shell side from passing through the pores of the hollow fibers.

The pressure of the inlet on the shell side was maintained at 1.5 psi and the outlet pressure of the feed side was set at 11.5 psi, thus maintaining a 10 psi differential between the two sides. In each of the runs, the feed flow was adjusted to give a flow rate of approximately 0.84 liter/min at these pressures. The typical feed solution volume for these experiments was 1 liter.

Samples from the feed solution and the strip dispersion were taken at timed intervals. The strip dispersion samples were allowed to stand until a phase separation occurred. The aqueous phase from the strip dispersion sample was then collected and centrifuged to facilitate complete separation. The aqueous phase samples from the strip dispersion samples and the feed solution samples were then analyzed by an ultraviolet (UV) spectrophotometer.

The flux of a species removed from the feed solution can be defined by the following formula:

$$\text{flux} = \frac{V \Delta C}{tA}$$

where V is the volume of the feed solution treated; $\Delta C$ is the concentration change in the feed solution; t is the time at which the sample is taken; and A is the membrane surface area. The flux of the species was calculated from the above equation.

The mass transfer coefficient k of the species removed from the feed solution can be defined by the following formula:

$$k = \frac{V}{tA} \ln\left(\frac{C_o}{C_t}\right)$$

where $C_o$ is the initial concentration of the species in the feed solution; $C_t$ is the concentration of the species in the feed solution at time t; t is the time; and the rest of the symbols are as defined above. The mass transfer coefficient k of the species was calculated from the above equation.

EXAMPLE 1

A strip dispersion was prepared by mixing together 200 ml of the 1.2 M sodium carbonate ($Na_2CO_3$) solution and 800 ml of an organic solution containing 10 wt. % N-lauryl-N-trialkylmethylamine with a molecular weight of 372 (a total number of 25.3 carbon atoms per amine molecule, e.g., Amberlite LA-2), 1 wt. % o-nitrophenyl octyl ether (o-NPOE), and 89 wt. % Isopar L as described in the general procedure above. The strip dispersion was fed into the shell side of a 2.5-inch polypropylene hollow fiber module. One liter of feed solution containing penicillin G at a concentration of 8,840 parts per million (ppm) was passed into the tube side of the hollow fiber module. The pH of the feed solution was maintained at 3 +/−0.1 by adding 3 M sulfuric acid as needed. Samples of the feed and strip solutions were collected at timed intervals and analyzed by UV as described in the general procedure above. Fluxes and k values were then calculated and are presented in the Table 1.

Penicillin G was removed from a high concentration of 8,840 ppm to a relatively low concentration of 1,161 ppm in the feed solution in 2.5 hours in the recycle mode of operation for both the feed solution and the strip dispersion. The penicillin G was recovered and concentrated to a high concentration of 40,802 ppm in the aqueous strip solution at the same time. This represented a recovery efficiency of 92.3%. After 4 hours of processing, the penicillin G was removed to a low concentration of less than 600 ppm in the feed solution, and it was recovered and concentrated to about 40,000 ppm in the aqueous strip solution. The results of the experiment are listed in Table 1 below. The penicillin G flux of 9.42 g/(m$^2$*hr) at the penicillin G concentration of 2,246 ppm in the feed solution was very high.

TABLE 1

| Penicillin G | | Amberlite | Strip Dispersion | | 1.2M Na$_2$CO$_3$ |
| --- | --- | --- | --- | --- | --- |
| Results Time (min.) | pH | LA-2 Strip (ppm) | Feed (ppm) | Feed Flux (g/(m$^2$*hr)) | k value (cm/sec) |
| 0 | 3 | 0 | 8,840 | | |
| 30 | | 4,256 | 2,246 | 9.42 | 0.00005430 |
| 60 | | 16,849 | 2,102 | 0.21 | 0.00000262 |
| 90 | | 32,725 | 1,772 | 0.47 | 0.00000676 |
| 120 | | 38,822 | 1,429 | 0.49 | 0.00000852 |
| 150 | | 40,802 | 1,161 | 0.38 | 0.00000822 |
| 180 | | 41,011 | 877 | 0.41 | 0.00001110 |
| 210 | | 38,370 | 722 | 0.22 | 0.00000770 |
| 240 | | 39,360 | 596 | 0.18 | 0.00000759 |

EXAMPLE 2

A strip dispersion was prepared by mixing together 200 ml of the 1.2 M sodium carbonate ($Na_2CO_3$) solution and 800 ml of an organic solution containing 10 wt. % N-lauryl-N-trialkylmethylamine with a molecular weight of 372 (a total number of 25.3 carbon atoms per amine molecule, e.g., Amberlite LA-2), 1 wt. % o-nitrophenyl octyl ether (o-NPOE), and 89 wt. % Isopar L as described in the general procedure above. The strip dispersion was fed into the shell side of a 2.5-inch polypropylene hollow fiber module. One liter of feed solution containing penicillin G at a concentration of 9,609 ppm was used. The pH of the feed solution was maintained at 4 +/− 0.1 by adding 3 M sulfuric acid as needed. Samples of the feed and strip solutions were collected at timed intervals and analyzed by UV as described in the general procedure above. Fluxes and k values were then calculated and are reported in Table 2.

Penicillin G was removed from a high concentration of 9,609 ppm to a concentration of 2,837 ppm in the feed solution in 2.5 hours in the recycle mode of operation for both the feed solution and the strip dispersion. Penicillin G was recovered and concentrated to a high concentration of 44,739 ppm in the aqueous strip solution at the same time. This represented a recovery efficiency of 83.6%. At the 5 hours in the recycle operation, the penicillin G was removed to a concentration of 1,540 ppm in the feed solution, and it was recovered and concentrated to a very high concentration of 55,064 ppm in the aqueous strip solution. This represented a recovery efficiency of 90.5%. The penicillin G flux at the penicillin G concentration of 6,499 ppm in the feed solution at pH 4 was 4.44 g/(m$^2$*hr), which was lower than the flux at pH 3 described in Example 1.

TABLE 2

| Penicillin G | | Amberlite | Strip Dispersion | | 1.2M Na$_2$CO$_3$ |
| --- | --- | --- | --- | --- | --- |
| Results Time (min.) | pH | LA-2 Strip (ppm) | Feed (ppm) | Feed Flux (g/(m$^2$*hr)) | k value (cm/sec) |
| 0 | 4 | 0 | 9,609 | | |
| 30 | | 11,861 | 6,499 | 4.44 | 0.00001550 |
| 60 | | 21,279 | 5,575 | 1.32 | 0.00000608 |
| 90 | | 32,109 | 4,378 | 1.71 | 0.00000957 |
| 120 | | 39,290 | 3,720 | 0.94 | 0.00000645 |
| 150 | | 44,739 | 2,837 | 1.26 | 0.00001070 |
| 180 | | 47,127 | 2,393 | 0.64 | 0.00000675 |
| 210 | | 49,296 | 1,948 | 0.64 | 0.00000814 |
| 240 | | 51,247 | 1,760 | 0.27 | 0.00000401 |
| 270 | | 53,736 | 1,710 | 0.07 | 0.00000116 |
| 300 | | 55,064 | 1,540 | 0.24 | 0.00000413 |

EXAMPLE 3

A strip dispersion was prepared by mixing together 200 ml of the 1.2 M sodium carbonate ($Na_2CO_3$) solution and 800 ml of an organic solution containing 10 wt. % N-lauryl-N-trialkylmethylamine with a molecular weight of 372 (a total nimber of 25.3 carbon atoms per amine molecule, e.g., Amberlite LA-2), 1 wt. % o-nitrophenyl octyl ether (o-NPOE), and 89 wt. % Isopar L as described in the general procedure above. The strip dispersion was fed into the shell side of a 2.5-inch polypropylene hollow fiber module. One liter of feed solution containing penicillin G at a concentration of 9,125 ppm was used. The pH of the feed solution was maintained at 5 +/−0.1 by adding 3 M sulfuric acid as needed. Samples of the feed and strip solutions were collected at timed intervals and analyzed by UV as described in the general procedure above. Fluxes and k values were then calculated and are reported in Table 3 below.

As reported in Table 3, the penicillin G was removed from a high concentration of 9,125 ppm to a concentration of 6,547 ppm in the feed solution in 2.5 hours in the recycle mode of operation for both the feed solution and the strip dispersion. Penicillin G was recovered and concentrated to a concentration of 7,434 ppm in the aqueous strip solution at the same time. This represented a recovery efficiency of 16.3%. At the 5 hours in the recycle operation, the penicillin G was removed to a concentration of 4,544 ppm in the feed solution, and it was recovered and concentrated to a concentration of 24,579 ppm in the aqueous strip solution. This represented a recovery efficiency of 53.9%. The penicillin G flux at the penicillin G concentration of 8,511 ppm in the feed solution at pH 5 was 0.88 g/(m$^2$*hr), which was lower than the flux values at pH 3 described in Example 1 and at pH 4 described in Example 2. Thus, the flux increased as the feed pH reduced.

TABLE 3

| Penicillin G Results Time (min.) | pH | Amberlite LA-2 Strip (ppm) | Strip Dispersion Feed (ppm) | Feed Flux (g/(m$^2$*hr)) | 1.2M Na$_2$CO$_3$ k value (cm/sec) |
|---|---|---|---|---|---|
| 0 | 4 | 0 | 9,125 | | |
| 30 | | 1,407 | 8,511 | 0.88 | 0.00000276 |
| 60 | | 2,380 | 7,792 | 0.77 | 0.00000259 |
| 90 | | 3,630 | 7,440 | 0.76 | 0.00000273 |
| 120 | | 4,117 | 6,896 | 0.78 | 0.00000301 |
| 150 | | 7,434 | 6,547 | 0.50 | 0.00000206 |
| 180 | | 10,422 | 6,264 | 0.40 | 0.00000175 |
| 210 | | 13,549 | 5,641 | 0.89 | 0.00000415 |
| 240 | | 18,551 | 5,271 | 0.53 | 0.00000269 |
| 270 | | 19,003 | 4,827 | 0.63 | 0.00000348 |
| 300 | | 24,579 | 4,544 | 0.40 | 0.00000239 |

What is claimed is:

1. A combined supported liquid membrane (SLM)/strip dispersion process for the removal and recovery of one or more target species selected from penicillin G, penicillin V, phenylalanine, acrylic acid, lactic acid, propionic acid, citric acid, acetic acid, and combinations thereof from a feed solution containing the target species comprising
   (1) treating a feed solution containing one or more target species on one side of the SLM embedded in a microporous support material to remove the target species by the use of a strip dispersion on the other side of the SLM, the strip dispersion being formed by dispersing an aqueous strip solution in an organic liquid comprising an extractant, using a mixer; and
   (2) allowing the strip dispersion or a part of the strip dispersion to separate into two phases, the organic liquid phase and the aqueous strip solution phase containing a concentrated solution of the target species.

2. The process of claim 1 wherein the penicillin is selected from the group consisting of penicillin G and penicillin V.

3. The process of claim 1, wherein the target species is penicillin G.

4. The process of claim 1 wherein the organic acid is selected from a group consisting of phenylalanine, acrylic acid, lactic acid, propionic acid, citric acid, acetic acid, and combinations thereof.

5. The process of claim 1 wherein the aqueous strip solution of the strip dispersion comprises a base.

6. The process of claim 5 wherein the base is selected from the group consisting of sodium carbonate (Na$_2$CO$_3$), sodium bicarbonate (NaHCO$_3$), sodium hydroxide (NaOH), ammonium hydroxide (NH$_4$OH), and tetramethylammonium hydroxide ((CH)$_4$NOH), and mixtures thereof.

7. The process of claim 1 wherein the organic liquid of the strip dispersion further comprises a modifier in a hydrocarbon solvent or mixture.

8. The process of claim 7 wherein the organic liquid of the strip dispersion comprises from about 2 wt. % to about 100 wt. % extractant and from about 0 wt. % to about 20 wt. % modifier in a hydrocarbon solvent or mixture.

9. The process of claim 8 wherein the organic liquid of the strip dispersion comprises from about 5 wt. % to about 40 wt. % extractant and from about 1 wt. % to about 10 wt. % modifier in a hydrocarbon solvent or mixture.

10. The process of claim 7 wherein the modifier is selected from the group consisting of alcohols, nitrophenyl alkyl ethers, trialkyl phosphates, and mixtures thereof.

11. The process of claim 10 wherein the alcohol is selected from the group consisting of hexanol, heptanol, octanol, nonanol, decanol, undecanol, dodecanol, tridecanol, tetradecanol, pentadecanol, hexadecanol, heptadacanol, octadecanol, and mixtures thereof.

12. The process of claim 10 wherein the nitro enyl alkyl ether is selected from the group consisting of o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether, and mixtures thereof.

13. The process of claim 10 wherein the trialkyl phosphate is selected from the grou consisting of tributyl phosphate, tris(2-ethylhexyl) phosphate, and mixtures thereof.

14. The process of claim 7 wherein the hydrocarbon solvent is selected from a group consisting of n-decane, n-undecane, n-dodecane, n-tridecane, n-tetradecane, isodecane, isoundecane, isododecane, isotridecane, isotetradecane, isoparaffinic hydrocarbon solvent, and mixtures thereof.

15. The process of claim 1 wherein the microporous support material is selected from the group consisting of polypropylene, polytetrafluoroethylene, polyethylene, polysulfone, polyethersulfone, polyetheretherketone, polyimide, polyamide, and combinations thereof.

* * * * *